US00PP07858P

United States Patent [19]

Kojima

[11] Patent Number: Plant 7,858

[45] Date of Patent: Apr. 28, 1992

[54] JAPANESE PLUM TREE AKIHIME

[75] Inventor: Shoichiro Kojima, Yuzawa, Japan

[73] Assignee: Nakajima Tenkoen Co., Ltd., Higashine, Japan

[21] Appl. No.: 484,086

[22] Filed: Feb. 23, 1990

[51] Int. Cl.[5] ..... A01H 5/00

[52] U.S. Cl. ..... Plt./38

[58] Field of Search ..... Plt. 38

[56] References Cited

PUBLICATIONS

Fogle, H. W. et al., "Plum" *North American and European Fruit and Tree Nut Germplasm Resources Inventory, U.S.D.A. Misc. Pub. No. 1406 (1981) pp. 412, 413.*

*Primary Examiner*—James R. Feyrer

*Attorney, Agent, or Firm*—Armstrong, Nikaido, Marmelstein, Kubovcik & Murray

[57] ABSTRACT

A Japanese plum tree characterized by high vigor and spreading tendency, producing a fruit which is round and very large (150–200 g) with a shallow suture and a short stalk, colored partially purplish red on yellow ground color with bloom. The fruit flesh is yellow, juicy, characterized by medium firmness, fine texture, high sugar content (Brix 13.65), and strong acidity (pH 3.5). The fruit ripens at mid-September, at approximately the same time as the known late-harvesting "Kelsey" variety of Japanese plum.

11 Drawing Sheets

BACKGROUND OF THE INVENTION

The invention involves a chance seedling which occurred as a volunteer plant in the inventor's orchard as will be described below. The new and distinct plum develops attractive, generally ovoid plums of larger than average, uniform size and symmetry. Fruit of the new variety is further characterized as having a harvest date of near that of "Kelsey", but wider and plumper than that of "Kelsey", and having an extensive purple-red blush covering a yellow-green ground skin color in variable pattern and degree. The skin is covered with a light to moderate surface bloom, and uniformly flecked with white conspicuous lenticels. Flesh is yellow (with no anthocyanin coloration) and is uniform in coloration throughout and is non-adherent to the stone which is quite small in comparison to the whole fruit. Having a sweet, rich taste, the fruit of the new variety, which has been named "Akihime" is expected to constitute an important addition to plums available to market after about mid-September.

The new variety of plum tree has been repeatedly asexually reproduced by placing buds of "Akihime", on plum seedlings. Such asexual reproductions have run true to the original discovery in every distinguishing respect by uniformly producing fruit of the character described herein. The genus and species of the new variety is *Prunus salicina.*

SUMMARY OF THE VARIETY

The invention is a Japanese plum tree variety "Akihime", which produces large fruit covered with purple red on a yellow ground color in mid-September. "Akihime" is distinguished from other Japanese plum varieties by its large fruit size, very late harvest time, and excellent taste.

BRIEF DESCRIPTION OF THE DRAWINGS

Each of FIGS. 1–4 is a photograph of the fruit of "Akihime".

Figure 1:
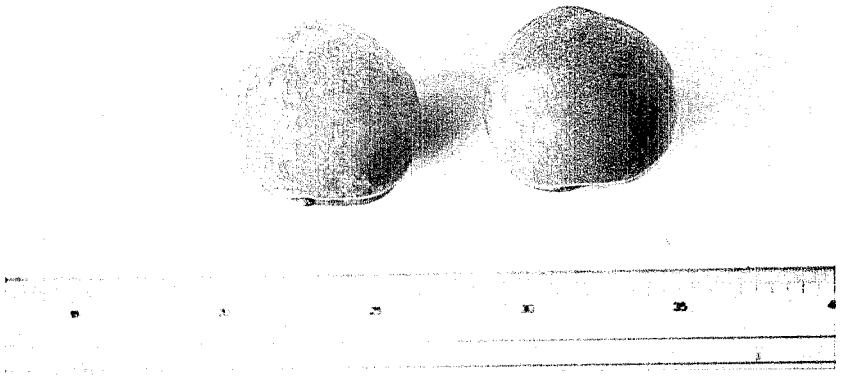
Figure 2:
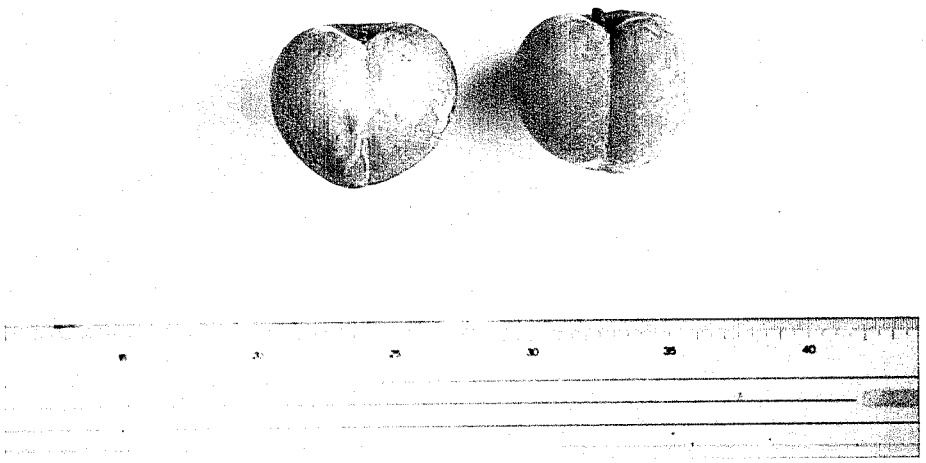
Figure 3:
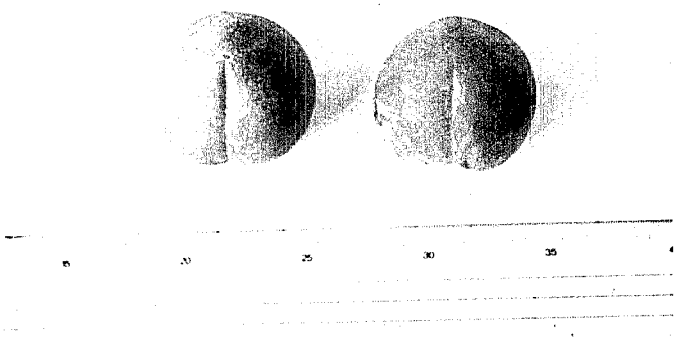
Figure 4:
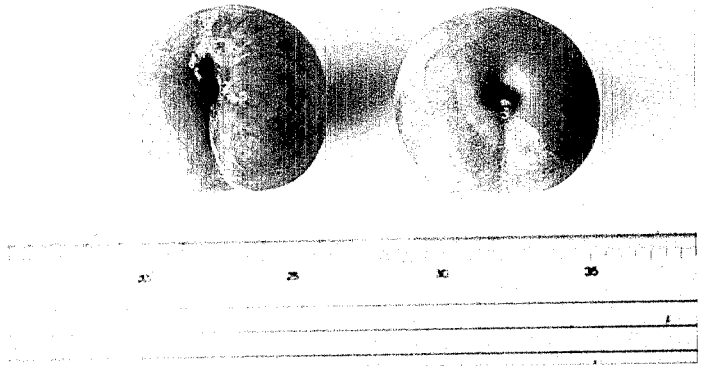
Figure 5:
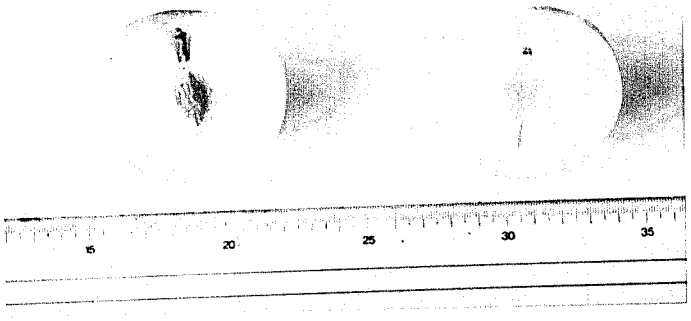
FIG. 5 is a photograph of a longitudinal section of "Akihime".
Figure 6:
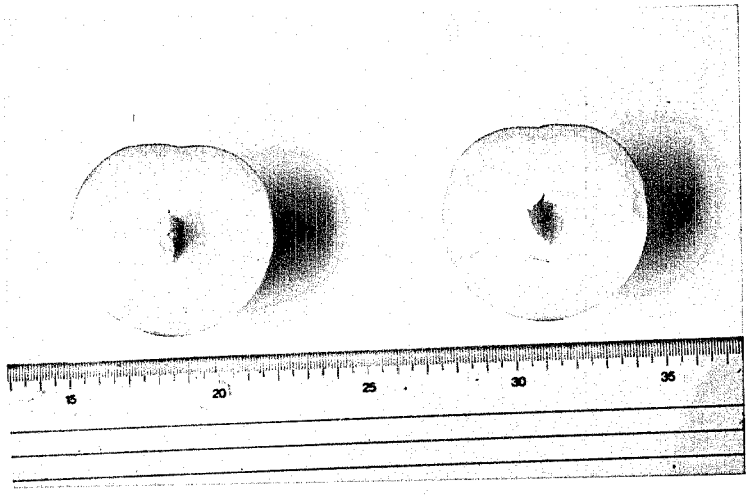
FIG. 6 is a photograph of a cross-section of "Akihime" fruit.
Figure 7:
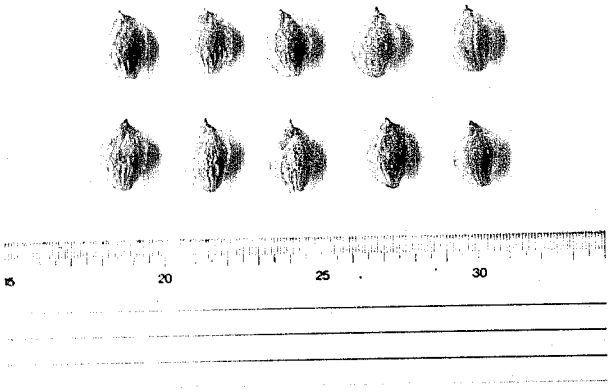
Figure 8:
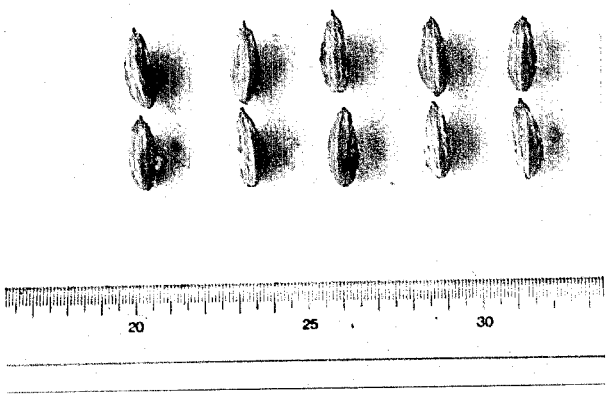
Figure 9:
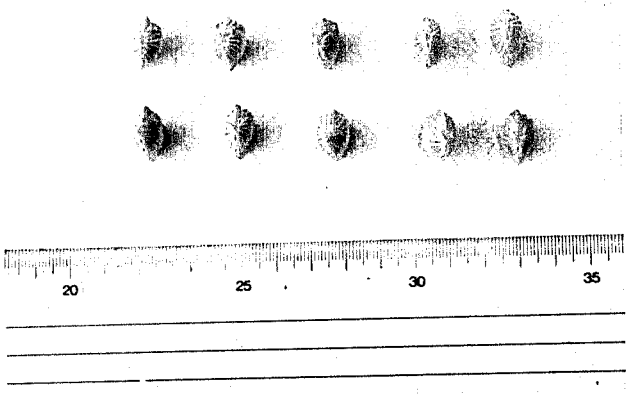

Each of FIGS. 7–9 is a photograph of a stone of "Akihime" fruit.

Figure 10:
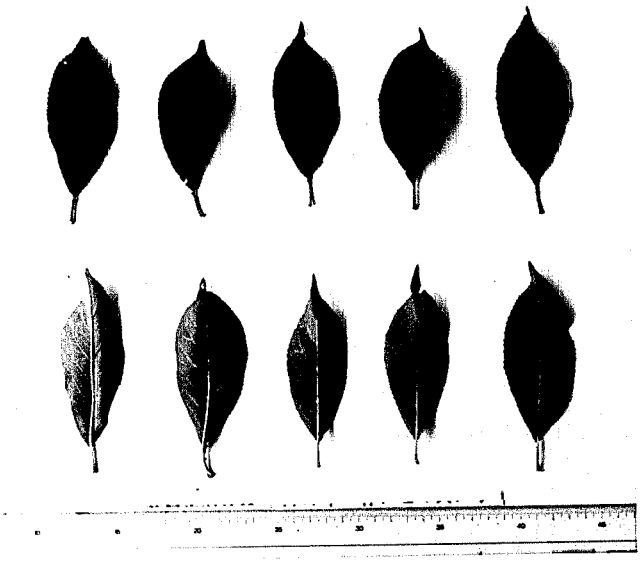

FIG. 10 is a photograph of leaves of "Akihime".

Figure 11:
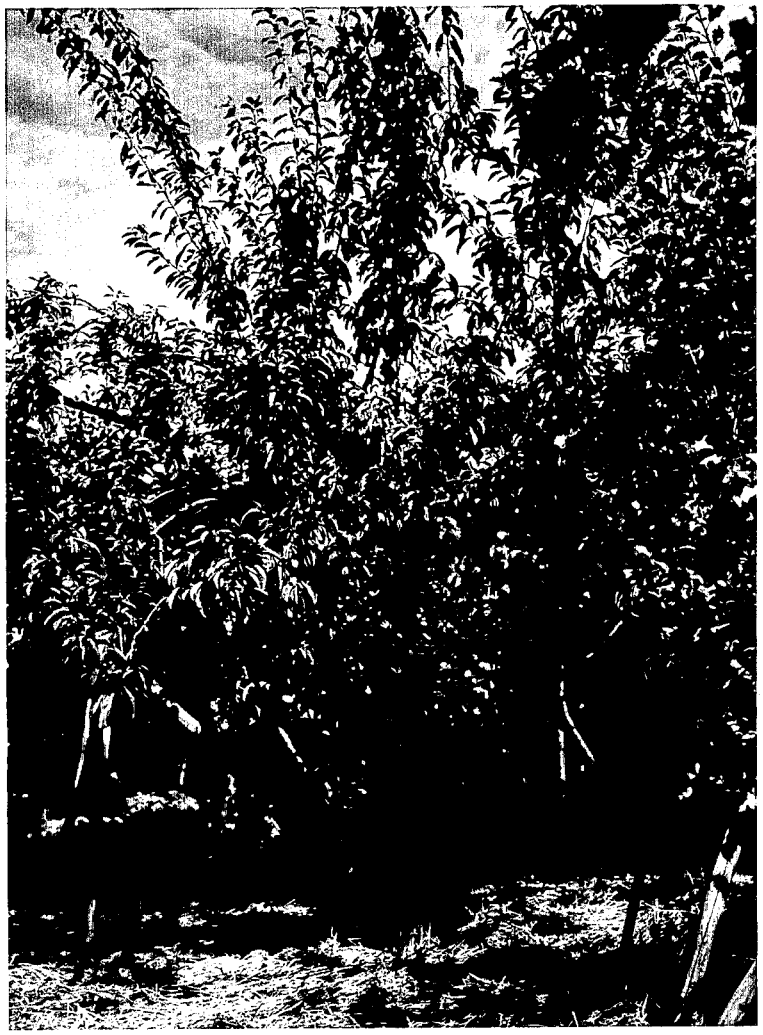

FIG. 11 is a photograph of the original tree of "Akihime".

Figure 12:
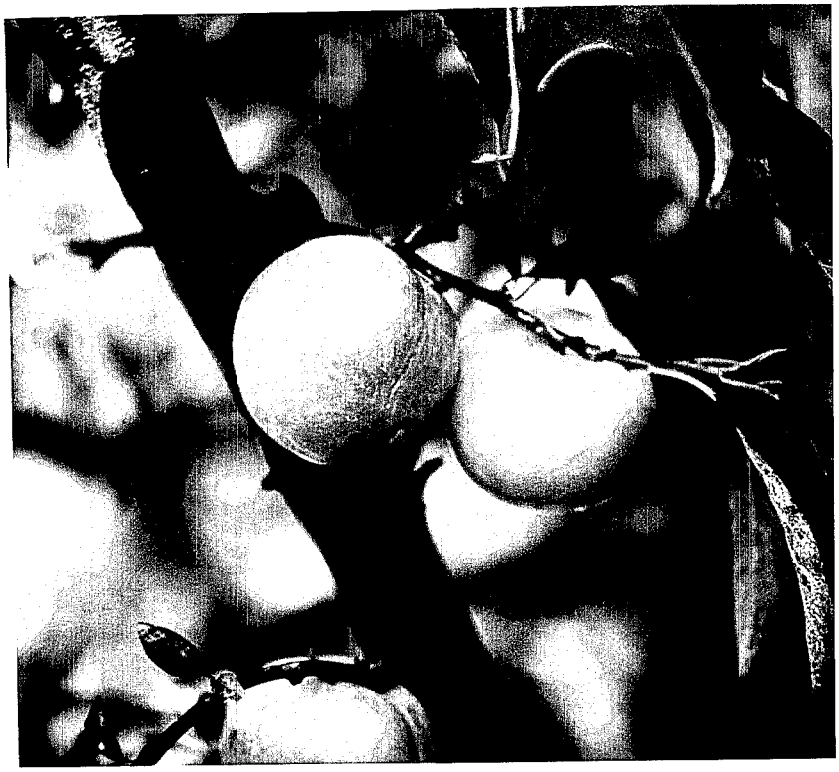
Figure 13:
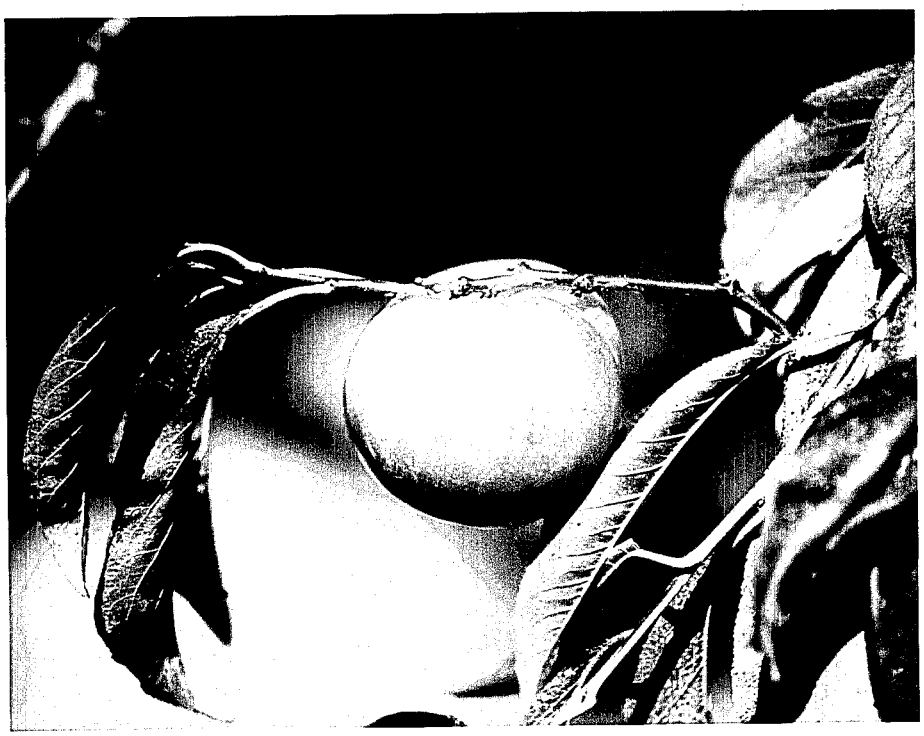

Each of FIGS. 12 and 13 is a photograph of the fruit of "Akihime".

Figure 14:
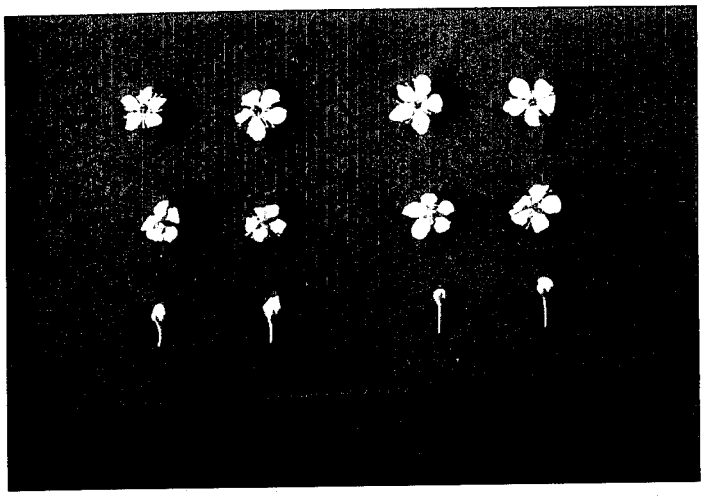

FIG. 14 is a photograph of flowers "Akihime" (left) compared with "Kelsey" flowers (right).

Figure 15:
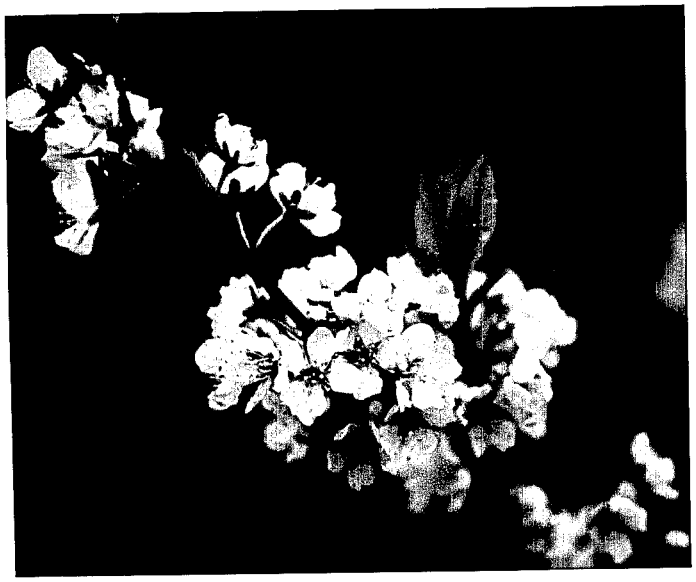

FIG. 15 is a photograph of flower clusters of "Akihime".

Figure 16:
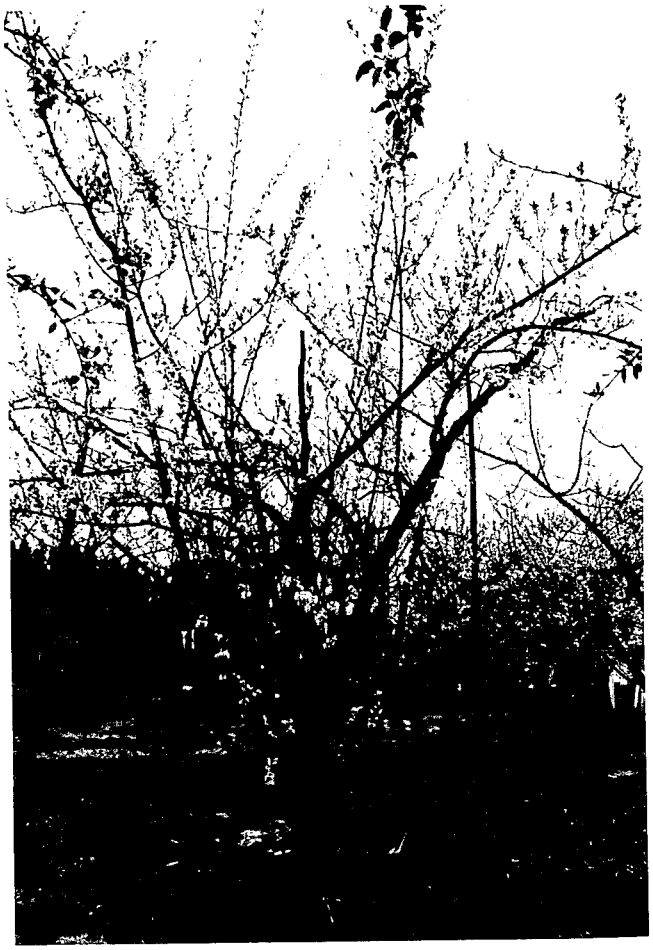

FIG. 16 is a photograph of the original tree of "Akihime".

Figure 17:
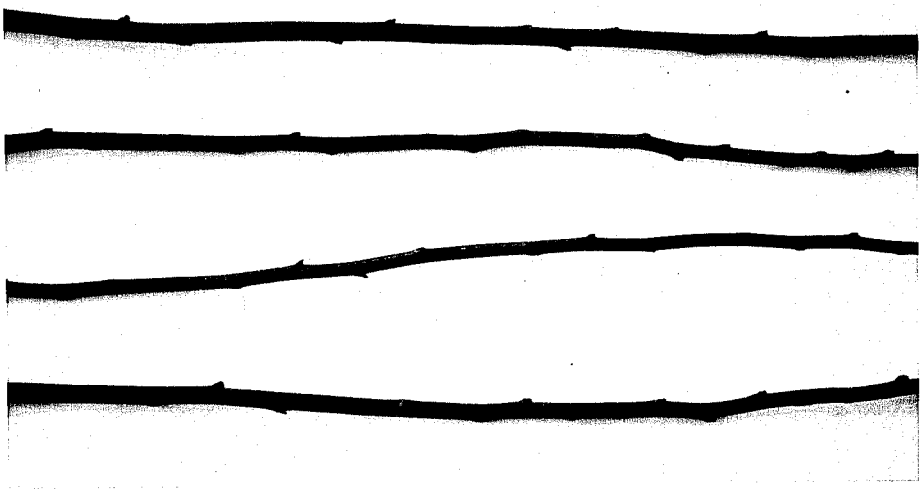

FIG. 17 is a photograph of a one-year shoot of "Akihime". The following is a description of the characteristics of the Japanese plum tree variety of this invention.

DESCRIPTION OF THE INVENTION

The plum tree variety of the invention was discovered by Shoichiro Kojima, in his orchard at No. 192, Iwanosawa, Aikawa, Sukawa, Yuzawa city, Akita prefecture, Japan, about 25 years ago. It was probably a chance seedling of Japanese plum dropped about 5 years earlier in the orchard. Mr. Kojima first cut off the young seedling. However, he subsequently left the stump alone from then on. The tree bore its first crop of fruit, which were very big, approximately 25 years ago. The productivity of the tree increased subsequently thereafter. Approximately 4 years ago, Mr. Kojima grafted budwoods of the original tree on plum seedlings. Fifteen trees of the Japanese plum variety of this invention, "Akihime", bore first crops in 1987. These trees when grafted on seedlings exhibited stability in retaining the characteristics of the original tree.

The Japanese plum tree variety of this invention, "Akihime", has approximately the same harvest time as the known "Kelsey" plum tree. However, "Akihime" differs from "Kelsey" in its fruit size, fruit skin color and fruit shape, as shown in the figures.

The following is a description of the characteristics of the Japanese plum tree variety of this invention.

Tree: Young tree is upright. However, it begins to spread upon bearing. Tree vigor is high. Tree size is medium. Tree height is slightly taller than width of tree canopy. Tree is affected by frost damage and productivity is slightly not stable.

Shoot: One-year old tree develops much feathering on current growth. ("Feathering" means much branching on current season shoot.) Color of one-year old shoot tip is strong brown (3YR 3/6) with no hairiness, and the bark at the base is a strong brown (6YR 2.5/5) with medium small lenticels. Dormant bud is small, pointed-shaped and held out from shoot. Bud support is small and not decurrent. Shoot is thick (diameter on one-year shoot is approximately 0.64 cm) with long internode (approximately 1.94 cm). Shoot color of surface exposed to the sun of current season shoot is red (Munsell 5R 2/6) and ground color of bark at base is yellow brown (Munsell 5YR 5/10). Anthocyanin coloration at shoot tip is absent.

Leaf: Leaf is small and elliptic, with acute tip, and wedge shape at base. Length of leaf blade is approximately 10.45 cm, width of leaf blade is approximately 4.36 cm, petiole is approximately 1.65 cm. Leaf margin is crenate without wave. Color of mature leaf is green (Munsell 5GY 3.5/5). Leaf is smaller than "Soldam" and with roundish reniform glands on both leaf base or pale scarlet petiole.

Fruit: Fruit is round to ovoid with slightly pointed apex and symmetric shape, and very large (150–200 g) with shallow suture. Depression of apex is indistinct. Stalk cavity is deep (approximately 1.0 cm) and wide (approximately 2.94 cm). Stalk is short (approximately 0.92 cm) and of medium thickness (approximately 0.24 mm). Fruit colors partially purplish red on yellow ground color with bloom. Skin color on the surface to the sun is pale purplish-red with bloom on yellow ground color. The skin is tenacious to flesh.

Flesh: Flesh is yellow, juicy, with fine texture. Taste is rich, with high sugar content (Brix 13.65) and strong acidity (pH 3.5). Firmness of flesh is medium. There is no anthocyanin coloring in the flesh or surface of stone. There is a small, hollow heart around the stone. The hollow heart is smaller than the hollow of "Kelsey". The flesh is fibrous.

Stone: Semi-free stone is small ellipse (length of approximately 2.28 cm, width of approximately 1.52 cm, thickness of approximately 0.90 cm), which is asymmetric with pointed apex and obtuse stalk end. Surface is pale yellowish brown and rough. The stone is pale orange-yellow (9YR 8.5/5) and there is no anthocyanin coloring on the surface.

Maturity: Fruit ripens at mid-September, at approximately the same time as "Kelsey" fruit. Blooming time is late April–early May at Akita, mid-season, about two days earlier than "Kelsey".

Flower: Flower is small (diameter of approximately 1.5 cm). Petal is small (length of approximately 1.0 cm, width of approximately 0.8 cm).

Fertilization: "Akihime" exhibits low self-fertilization and requires a pollenizer like "Oishi Wase", etc.

Usage: To be used as a dessert plum. It is not used for dry fruit.

Storage: It can be stored 7–10 days in cold storage.

I claim:

1. A new and distinct variety of Japanese plum tree, substantially as illustrated and described herein, particularly characterized by producing large fruit covered with purple red on a yellow ground color, maturing as late as the known late-harvesting "Kelsey" variety of Japanese plum tree.

* * * * *